(12) United States Patent
Nagamine et al.

(10) Patent No.: US 7,074,907 B2
(45) Date of Patent: Jul. 11, 2006

(54) COMPOUND, PROCESS FOR PRODUCING THE SAME AND USE THEREOF

(75) Inventors: Kenichi Nagamine, Tokyo (JP); Miki Hayashi, Tokyo (JP); Kaori Yamasaki, Nagasaki (JP)

(73) Assignee: Nichirei Biosciences Inc., Tokyo (JP)

( * ) Notice: Subject to any disclaimer, the term of this patent is extended or adjusted under 35 U.S.C. 154(b) by 0 days.

(21) Appl. No.: 10/543,801

(22) PCT Filed: Dec. 24, 2003

(86) PCT No.: PCT/JP03/16544

§ 371 (c)(1),
(2), (4) Date: Jul. 29, 2005

(87) PCT Pub. No.: WO2004/074304

PCT Pub. Date: Sep. 2, 2004

(65) Prior Publication Data

US 2006/0104927 A1 May 18, 2006

(30) Foreign Application Priority Data

Feb. 20, 2003 (JP) .............................. 2003-042486

(51) Int. Cl.
*C09K 15/08* (2006.01)
*C07H 15/203* (2006.01)
*A61K 31/7032* (2006.01)
*A23B 7/08* (2006.01)

(52) U.S. Cl. .................. 536/18.2; 252/404; 426/268; 514/25

(58) Field of Classification Search ............... 536/18.2; 252/404; 426/268; 514/25
See application file for complete search history.

(56) References Cited

FOREIGN PATENT DOCUMENTS

JP 2001-031580 2/2001

OTHER PUBLICATIONS

Sandoval, Manuel et al., "Antioxidant and biological properties of *Myrciaria dubia*: Role in cytoprotection" Free Radical Biology and Medicine, Nov. 2001, vol. 31, Issue 10, Supplement 1, pg. S37.

Machida, Koichi et al., "Studies on the Constituents of *Catalpa* Species. VI. Monoterpene Glycosides from the Fallen Leaves of *Catalpa ovata* G. Don" Chemical and Pharmaceutical Bulletin, Jun. 2001, vol. 49, No. 6, pp. 732-736.

*Primary Examiner*—Bernard Dentz
(74) *Attorney, Agent, or Firm*—Darby & Darby

(57) ABSTRACT

The compound of the present invention is a component originated from a natural material, camu camu (*Myrciaria dubia*), has strong antioxidative activity and stable whitening effect, and is represented by the formula (1). The antioxidant, whitening agent, skin preparation for external use, cosmetics, and food of the present invention are characterized by the inclusion of the compound represented by the formula (1)

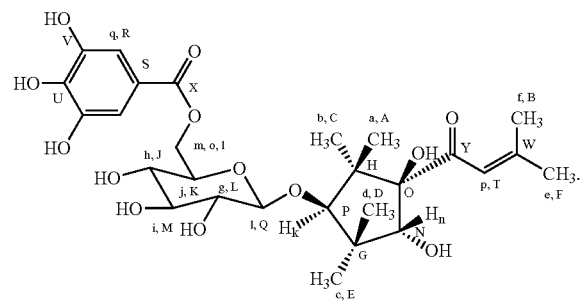

7 Claims, 2 Drawing Sheets

Measurement of Linoleic acid autooxidation inhibitory effect
Comparative Experiments at 0.01 % (w/v)

Rate of linoleic acid autooxidation after 2 weeks (%)
Comparative experiments at 0.01 %(w/v)

COMPOUND, PROCESS FOR PRODUCING THE SAME AND USE THEREOF

This application is a national stage entry of PCT/JP03/16544 filed Dec. 24, 2003.

FIELD OF ART

The present invention relates to a novel compound obtained from, for example, camu camu (*Myrciaria dubia*), a fruit tree of the genus *Myrciaria* of the family Myrtaceae, which compound has antioxidative activity and whitening effect, and is useful for cosmetics, food and drink, as well as a method for producing the compound and use of the compound.

BACKGROUND ART

In recent years, there are growing fears about health hazards of materials of animal origin, and regulations for such materials are being tightened, which gives rise to stronger interest in materials of plant origin in cosmetic industries. On the other hand, serious problems are arising, such as acceleration of ageing by oxidation of active oxygen taken into or generated within the body, and skin coloration by UV rays or carcinogenicity thereof.

Cosmetics, dermatological compositions, and food compositions are suffering from oxidation or peroxidation of oils and fats contained in various materials thereof, during processing, manufacture, storage, or preservation of such articles. Unsaturated fatty acids contained in oils and fats, such as linoleic and linolenic acids, are known to be particularly prone to peroxidation by atmospheric oxygen to generate lipid peroxides, free radicals, or even carcinogenic substances (see, for example, "Shokuhin no Housou" Vol. 17, p 106, 1986). Oxidation and peroxidation cause change of the products in appearance, such as coloration, discoloration, denaturalizaton, or abnormal odor, or in quality, such as decrease in effective nutritional value or effectiveness. Further denaturalization may cause generation of toxic substances, which results in deterioration of product quality.

In order to inhibit such oxidation and peroxidation of unsaturated fatty acids, and to prevent deterioration of product quality, various antioxidants have conventionally been used. Antioxidants act on peroxide radicals, which are generated in oxidation, to terminate chain oxidation, or alternatively act on free radicals to terminate oxidative reaction. Commonly used antioxidants are synthetic antioxidants, such as butylhydroxyanisol (BHA) and butylhydroxytoluene (BHT). Recently, however, effects and safety of synthetic antioxidants on the human body have come to be questioned as their use expands, and consumers are presenting growing rejections.

This situation leads to rapidly growing expectation for natural antioxidants. However, known natural antioxidants, such as natural vitamin E ($\alpha$-tocopherol), vitamin C, and the like, have disadvantages in that their activity cannot be maintained stably for a prolonged period of time. Accordingly, there is a strong demand for natural antioxidants having strong antioxidative activity as well as long-term stability in the activity.

In the cosmetic industry, whitening effect on skin has been an important issue, which has been attracting various proposals to date. Causes of pigmentation, such as skin coloration or age spots, may be categorized roughly into intrinsic factors such as metabolic defects in living organism, and extrinsic factors such as UV rays. Pigmentation caused by the latter extrinsic factors is more common, wherein UV rays stimulate melanocytes to activate the same, which in turn activates tyrosinase to induce skin pigmentation. Inhibition of the melanocyte activity to thereby inhibit generation of tyrosinase and melanin pigment results in prevention of pigmentation such as skin coloration or age spots, and accordingly maintenance of white skin. Recently, UV dose is increasing due to ozone depletion, which further stimulates consumer's demand for measures against UV, and safe and effective whitening agents.

Camu camu fruit is rich in vitamin C, and is now recognized as the most vitamin C-rich plant. The fruit of camu camu is commercially sold in South America as cosmetics or food, and is recently imported and sold also in Japan as a food material. Vitamin C is the only component of the fruit of camu camu that is known to have antioxidative effect and whitening effect.

SUMMARY OF THE INVENTION

It is therefore an object of the present invention to provide a novel compound of natural origin having strong antioxidative activity and stable whitening effect, as well as a method for producing the compound, and an antioxidant, a whitening agent, skin preparations for external use, cosmetics, and food.

According to the present invention, there is provided a compound represented by the formula (1) (referred to as compound CA-1 hereinbelow):

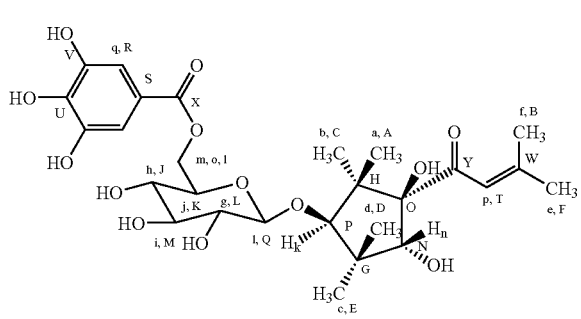

According to the present invention, there is also provided a method for producing the compound CA-1 comprising preparing an extract from one or more materials selected from the group consisting of camu camu fruit juice, camu camu fruit pericarp, camu camu seeds, and mixtures thereof using water and/or an organic solvent, and purifying the extract.

According to the present invention, there is also provided an antioxidant or a whitening agent comprising the compound CA-1 as an active component.

According to the present invention, there is further provided a skin preparation for external use or cosmetics comprising the above-mentioned antioxidant and/or whitening agent.

According to the present invention, there is also provided food comprising the above-mentioned antioxidant.

PREFERRED EMBODIMENTS OF THE INVENTION

Figure 1:
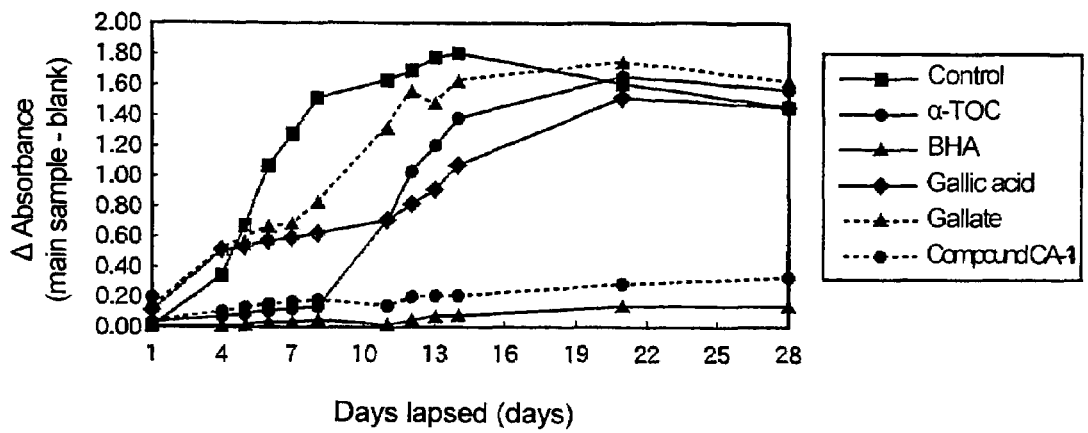
FIG. 1 is a graph showing the results of the test for linoleic acid autooxidation inhibitory effect conducted in Example 2.

The present invention will now be explained in detail.

Compound CA-1 of the present invention is represented by the formula (1), and has antioxidative activity and whitening effect as will be discussed later.

The physicochemical properties of the compound CA-1 are as follows: mass spectrum: m/z593$[M+Na]^+$; molecular formula: $C_{27}H_{38}O_{13}$; ultraviolet absorption spectrum: $\lambda_{max}$m(MeOH): 217 nm, 248 nm; $^1$H-NMR chemical shift: δppm(599.6 MHz, solvent $CD_3OD$); 7.08(s,H-q), 6.61(s,H-p), 4.53(H-o,J=11.8), 4.49(s,H-n), 4.40(H-m,J=11.8), 4.28 (d,H-1,J=7.8), 3.82(s,H-k), 3.52(H-j,J=6.4,2.0), 3.38(m,H-i), 3.37(m,H-h), 3.23(H-g,J=8.7), 2.10(s,H-f), 1.92(s,H-e), 1.13(s,H-d), 1.05(s,H-c), 0.97(s,H-b), 0.73(s,H-a); $^{13}$C-NMR chemical shift: δppm(150.8 MHz, solvent $CD_3OD$); 203.5(C-Y), 168.4(C-X), 157.8(C-W), 146.5(C-V), 139.9 (C-U), 122.6(C-T), 121.6(C-S), 110.4(C-R), 105.6(C-Q), 95.7(C-P), 90.1(C-O), 80.0(C-N), 78.3(C-M), 75.7(C-L), 75.4(C-K), 72.1(C-J), 65.0(C-I), 46.8(C-H), 42.2(C-G), 28.2 (C-F), 26.9(C-E), 26.4(C-D), 21.5(C-C), 21.1(C-B), 20.2(C-A).

The compound CA-1 of the present invention may be obtained, for example, by a method including preparing an extract from fruit juice, fruit pericarp, and/or seeds of camu camu (*Myrciaria dubia*), which is a fruit tree of the genus *Myrciaria* of the family Myrtaceae, using water and/or an organic solvent, and purifying the extract. For example, camu camu seeds may be subjected to extraction with a solvent, and the resulting extract liquid may be concentrated and then purified by liquid—liquid separation, chromatography, or the like process, to thereby obtain a purificate of not lower than 95% purity.

The extractant may be, for example, water and/or an organic solvent. The organic solvent may either be a hydrophilic or hydrophobic organic solvent.

The hydrophilic organic solvent may be a conventional organic solvent, for example, alcohols such as methyl alcohol, ethyl alcohol, glycerin, propylene glycol, and 1,3-butylene glycol; acetone, tetrahydrofuran, acetonitrile, 1,4-dioxane, pyridine, dimethylsulfoxide, N,N-dimethylformamide, and acetic acid.

The hydrophobic organic solvent may be a conventional organic solvent, such as hexane, cyclohexane, carbon tetrachloride, chloroform, dichloromethane, 1,2-dichloroethane, diethyl ether, ethyl acetate, benzene, or toluene. One or a combination of two or more of these extractants may be used.

The conditions for extraction are not particularly limited. For example, the temperature may be 5 to 95° C., preferably 15 to 85° C., and even the room temperature will give good extraction. The extraction time may be a few hours to a few days, and the amount of the extractant is usually 1 to 50 times, preferably 5 to 25 times the amount of the raw material by weight.

The extraction operation is not particularly limited, and may be performed according to a common procedure. For improving the extraction efficiency, the extraction may be performed under shaking, or in an extraction device equipped with a stirrer or the like. For example, camu camu fruit or seeds and an extractant may be stirred and shaken together, with or without preliminary soaking of the fruit or seeds in the extractant, and the resulting process liquid may be subjected to filtration, centrifugation, or decantation to separate the extract liquid from the extract residue. The extract residue may further be subjected to a similar extraction process. The obtained extract liquid may be use as it is for separation and purification, or may further be concentrated as desired before separation and purification.

The concentration process is not particularly limited, and may be performed by, for example, solvent removal, recovery of soluble components by making use of their solubility in water and/or an organic solvent, liquid—liquid separation with a water-hydrophobic organic solvent, recrystallization, reprecipitation, recovery of precipitate formed by cooling, or a combination of two or more of these.

The purification process is not particularly limited, and may be performed by, for example, normal and/or reverse phase chromatography to obtain a purificate.

The compound CA1 of the present invention, when prepared by the above-mentioned extraction operation, may not necessarily be a pure product for the various purposes to be discussed later, and may be in the form of a variety of crude purificates obtained from the purification process. For example, crude purificates containing the compound CA1 of the present invention at not less than 90 wt %, not less than 95 wt %, or further not less than 98 wt %, or even not less than 99 wt % may be used.

The antioxidant and the whitening agent of the present invention contain the compound CA1 of the present invention as an active component.

In the antioxidant and the whitening agent of the present invention, the content of the compound CA1 of the present invention as an active component, may suitably be selected depending on its form of use for achieving its effect.

The skin preparation for external use and the cosmetics according to the present invention are not particularly limited as long as they contain the antioxidant and/or the whitening agent of the present invention. The type of the cosmetics is not particularly limited, and may be, for example, skin care cosmetics such as skin lotion, emulsion, cream, face pack, and cleansing agents; make-up cosmetics such as lipsticks and foundation; or hair cosmetics. The cosmetics may be in any form without limitation. The skin preparation for external use may be, for example, ointment or various dermatological agents.

In the present skin preparation for external use and the cosmetics, the content of the present antioxidant and/or the whitening agent may suitably be selected depending on their kind, the kind and amount of other components to be mixed, and the form of the agent. Usually, the content is 0.0001 to 2 wt %, preferably 0.001 to 1 wt % of the total amount of the skin preparation for external use or the cosmetics, in terms of the compound CA1 of the present invention (at not lower than 95% purity).

The skin preparation for external use or the cosmetics according to the present invention may optionally contain various other components usually used as raw materials for cosmetics, as long as the desired effects of the present invention are not impaired. Examples of such other components may include water, oil solutions, surfactants, lubricants, alcohols, water-soluble polymeric agents, gelatinizers, moisture retainers, buffers, preservatives, antiinflammatory agents, thickeners, flavoring agents, vitamins, and antioxidants and whitening agents other than the compound CA1 of the present invention. These may suitably be selected and combined for use, depending on the kind and other purposes of the skin preparation for external use and cosmetics, and also on the form thereof.

Food according to the present invention is not particularly limited as long as it contains the antioxidant of the present invention. The food may be of any type, for example, candies, beverages, jam, or chewing gum. The food may be in any form without limitation.

In the food of the present invention, the content of the present antioxidant may suitably be selected depending on the kind of the food, or the kind and amount of other components contained in the food. Usually, the content is 0.0001 to 1 wt %, preferably 0.001 to 0.1 wt % of the total amount of the food, in terms of the compound CA1 of the present invention (at not lower than 95% purity).

The food according to the present invention may optionally contain various other components usually used as raw materials for food, as long as the desired effects of the present invention are not impaired. Examples of such other components may include water, alcohols, sweeteners, acidulants, colorants, preservatives, flavoring agents, and excipients. These may suitably be selected and mixed depending on the kind and other purpose of the food, or on the form thereof.

Since the present compound may be extracted and purified from a natural material originated from camu camu fruit, the compound has excellent safety. The present compound also has excellent antioxidative activity and whitening effect, so that it is useful as an antioxidant and a whitening agent. The antioxidant and the whitening agent of the present invention have strong antioxidative activity and inhibitory effect on melanin formation, and the antioxidative activity against oil-soluble components is superior to that of gallic acid. Thus, the antioxidant and the whitening agent of the present invention may be applied to skin preparation for external use or cosmetics, expecting the whitening effect and antioxidative activity, or may also be applied to food, expecting the quality improvement and preventive effects against oxidation.

EXAMPLES

The present invention will now be explained in more detail with reference to Examples, which are illustrative only and do not intend to limit the present invention.

Example 1

6000 g of crushed camu camu seeds were mixed with methanol of 14 times the weight of the camu camu seeds, and stirred overnight at 25° C. for extraction. The entire mixture was centrifuged at 5° C. at 4000 rpm for 45 minutes, coarsely filtered, and then passed through a 0.22 µm filter. The obtained filtrate was concentrated and evaporated to dry to obtain 387.63 g of an extract. The extract was dissolved in 3600 ml of purified water, and subjected to serial liquid—liquid separation three times with n-hexane and seven times with ethyl acetate. The obtained ethyl acetate fractions were vacuum concentrated to obtain 12.89 g of a concentrate. Next, this concentrate was re-dissolved in ethyl acetate, and applied to a column of silica gel (Wakosil C-300, manufactured by WAKO PURE CHEMICAL INDUSTRIES, LTD.) to elute in sequence with chloroform/methanol mixtures of increasing methanol content with respect to chloroform of 10:0, 9:1, 8:2, 7:3, 6:4, 5:5, and 2:8. The fractions eluted with 8:2 to 7:3 chloroform/methanol mixed solvents were collected and vacuum concentrated. The resulting concentrate was dissolved in purified water, and applied to a C18 column. The methanol fractions were collected, vacuum concentrated, and dissolved in 5 ml of methanol.

Next, the resulting mixture was further purified by preparative high performance liquid chromatography (HPLC), wherein the mixture was first coarsely purified under the elution condition (1) specified below, and then under the conditions (2) and (3), respectively, to obtain a purificate of not lower than 95% purity. The conditions for HPLC are specified below. The resulting purificate was subjected to measurements of mass spectrum, ultraviolet absorption spectrum, $^1$H-NMR spectrum, and $^{13}$C-NMR spectrum. It was confirmed that the results of the measurements were identical with the physicochemical properties mentioned above, so that the obtained compound was compound CA1 represented by the formula (1).

Column: Inertsil ODS-3[20×250 mm] (GL-Science Inc.); Flow rate: 8 ml/min.; Temperature: 40° C.; Detection: UV at 257 nm; Elution solvent: A) water, B) acetonitrile;

(1) 15% B (0–10 min.), 15–30% B (10–110 min., linear), 30–110% B (110–120 min., linear);

(2) 20% B (0–20 min.), 20–30% B (20–70 min., linear);

(3) 30% B (0–35 min.).

Example 2

Using the compound CA1 of not lower than 95% purity of the present invention obtained in Example 1, the following test for linoleic acid autooxidation inhibitory effect was conducted.

<Test for Linoleic Acid Autooxidation Inhibitory Effect>

2 ml of 2.5% (w/v) linoleic acid was mixed with 4 ml of a 0.05 M phosphate buffer (pH 7.0) to prepare a reaction liquid. The compound of the present invention was dissolved in 99.5% ethanol at a concentration of 0.01% (w/v) 2 ml of the resulting solution and 2 ml of distilled water were added to the reaction liquid to make the total volume to 10 ml, mixed, and placed in a brown threaded bottle to prepare a sample.

A negative control was prepared by adding, to the reaction liquid, only 2 ml of 99.5% ethanol and 2 ml of distilled water, without adding anything else. Positive controls were prepared in the same way as for the present compound at the same concentration, except that the present compound was replaced with α-tocopherol or BHA.

The samples prepared above were stored in darkness at 40° C. as main samples, and in darkness at 4° C. as blanks, and the measurements were made at intervals for 4 weeks.

The measurement was carried out by mixing 0.1 ml of a sample, 9.7 ml of 75% ethanol, and 0.1 ml of a 30% ammonium thiocyanate solution, adding 0.1 ml of $2 \times 10^{-2}$ M ferrous chloride (3.5% hydrochloric acid solution) thereto, and exactly 3 minutes later, measuring the absorbance at 500 nm. From the measured values, the difference in absorbance and the rate of autooxidation after two weeks were obtained. The same measurement was made with the blanks, and ΔAbsorbance=(Absorbance of Main Sample)−(Absorbance of Blank) was taken. The results are shown in FIG. 1.

The absorbance increases with oxidation of the sample, and after reaching the maximum, decreases with consumption of the sample to be oxidized. Thus earlier occurrence of the peak absorbance represents weaker antioxidative activity.

Figure 2:
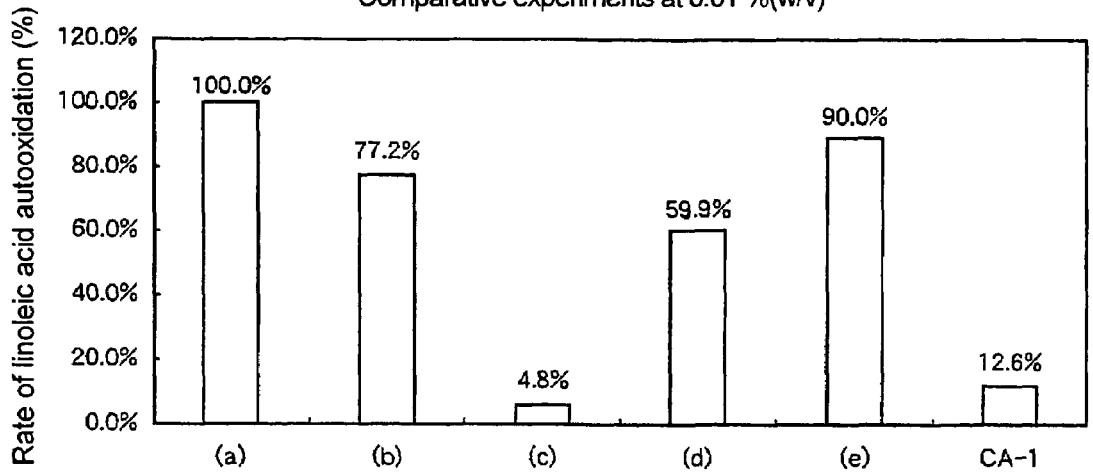
FIG. 2 is a graph showing the degree of oxidation of each sample measured after two weeks in the test for linoleic acid autooxidation inhibitory effect conducted in Example 2.

Further, the antioxidative activities of the samples were compared in terms of the degree of oxidation. The degree of oxidation was calculated according to the following formula, with the oxidation of the control (absorbance) on the day after two weeks of the test being 100%. The results are shown in FIG. 2. Incidentally, in FIGS. 2, (a), (b), (c), (d), and (e) represents the control, the sample with α-TOC, the sample with BHA, the sample with gallic acid, and the sample with a gallate, respectively, and CA-1 represents the sample with the compound of the present invention.

Degree of Linoleic Acid Autooxidation (%)=([ΔAbsorbance of Sample]/[ΔAbsorbance of Control])×100

A higher value of the degree of oxidation represents lower antioxidative activity. It is understood from the experiments that the present compound has antioxidative activity that is stronger than that of a known natural antioxidant, α-tocopherol, and comparable to that of a synthetic antioxidant, BHA. Further, the present compound has a gallic acid structure in a portion of its molecular structure. However, it is understood from the above comparison that the gallic acid and its salt per se have weaker oxidation inhibitory effect on linoleic acid, and thus the antioxidative activity on linoleic acid is peculiar to the present compound. This is assumed to be ascribable to the higher hydrophobicity of the present compound compared to the gallic acid. Thus the present compound is useful as an antioxidant for the components contained in cosmetics, skin preparations for external use, and food, in particular, oils and fats.

Example 3

The antioxidative activity of the compound of not lower than 95% purity of the present invention prepared in Example 1 was evaluated using a stable radical, 1,1-diphenyl-2-picrylhydrazyl (DPPH).

To 1600 μl of 250 mM acetate buffer (pH=5.5), 1200 μl of ethanol and 400 μl of a sample (at an arbitrary concentration in ethanol) were mixed, and pre-incubated at 30° C. for 5 minutes. 800 μl of a 500 μM DPPH/ethanol solution was added, mixed, and left to stand at 30° C. for 30 minutes. Then the absorbance of the sample at 517 nm was measured.

A negative control was prepared by adding, instead of the sample solution, only ethanol to the reaction liquid without adding anything else. A positive control was prepared in the same way as for the present compound at the same concentration in ethanol, except that the present compound was replaced with α-tocopherol. From the measured absorbances, the radical scavenging ratio was calculated in accordance with the following formula. The results are shown in Table 1.

Scavenging ratio (%)=(1−[Absorbance of Sample]/[Absorbance of Control])×100

The scavenging ratios were measured with the sample concentration in the sample solution being changed stepwise, to determine the concentration of the sample solution at which the DPPH radical scavenging ratio was 50%. This concentration was taken as the 50% DPPH radical scavenged concentration. A lower value of this concentration represents higher radical scavenging activity.

TABLE 1

| Sample Measured | 50% DPPH radical scavenged concentration (μg/ml) |
|---|---|
| Compound of Present Invention | 90.9 |
| α-tocopherol | 121.5 |

As shown in Table 1, it has been demonstrated that the compound of the present invention is comparable to or even higher than α-tocopherol in radical scavenging activity.

Example 4

The compound CA1 of the present invention prepared in Example 1 was tested for whitening effect at cellular level, using murine B16 melanoma cells. By the use of animal cells, this test allows confirmation of the inhibitory effect on melanin formation and the effect on cell proliferation in an environment similar to that within the living body.

Petri dishes were seeded with $1 \times 10^5$ cells/ml of murine B16 melanoma cells, and cultured at 37° C. in 5% $CO_2$ for 2 days. After the culture solution was removed, 10 ml/dish of a test medium adjusted with the compound CA1 of the present invention, 10% FBS/DME medium as a blank, or a medium adjusted with gallic acid as a control, which is a component isolated from camu camu seeds, was added to each petri dish, and cultured at 37° C. in 5% $CO_2$ for 3 days. After the culture solution was removed, the cells were dissociated with a trypsin solution, centrifuged, suspended in PBS, and centrifuged again. The supernatant was removed, and the remaining cell pellet was mixed with a sodium hydroxide solution. The mixture was heat-treated to dissolve the melanin pigment, and fibrous materials derived from the cells were filtered out. The resulting solution was measured for the dissolved melanin pigment by means of an absorptiometer, and for a protein content by means of a DC-Protein Assay KIT manufactured by BIO-RAD.

The inhibitory effect of each sample on melanin formation was calculated by the following formula, taking the inhibitory effect of the blank medium on melanin formation as 0% as a control. The results are shown in FIG. 3.

Ratio of Inhibition of Melanin Formation (%)=100−([Average Melanin Amount per 1 mg of Total Protein of Sample]/[Average Melanin Amount per 1 mg of Total Protein of Control])×100

Figure 3:
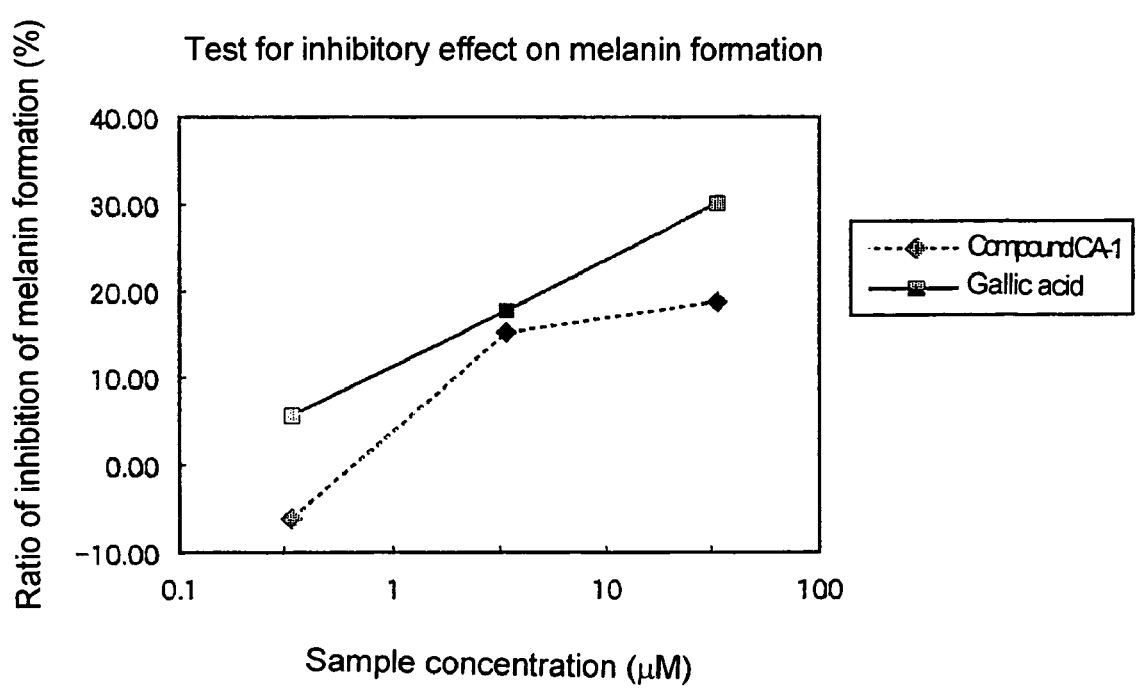
FIG. 3 is a graph showing the results of the test for inhibition of melanin formation conducted in Example 4.

From FIG. 3, it is understood that the compound CA1 of the present invention is comparable to gallic acid in inhibitory effect on melanin formation. In the results of this experiment, the present compound was slightly lower than gallic acid in the ratio of inhibition of melanin formation. However, when the present compound is used in cosmetics and skin preparations for external use, which are often in the form of emulsion or cream, it is believed that the present compound is more advantageous than gallic acid in mixing and stability due to its higher hydrophobicity.

Further, since the total protein amount is in proportion to the cell count, the total protein amount of each test medium was measured, and its effect on cell proliferation was tested. As a result, no remarkable difference was observed in total protein amount of the samples. Further microscopic observation revealed no problem.

Prescription Example 1

0.20 parts by weight of dipotassium glycyrrhizinate, 0.10 parts by weight of citric acid, 0.30 parts by weight of sodium citrate, 0.01 parts by weight of the compound purified in Example 1, and 5.00 parts by weight of 1,3-butylene glycol were mixed, and purified water was added to increase the total amount to 80.0 parts by weight. The mixture was dissolved under stirring at 50° C. to prepare an aqueous solution containing the present compound.

0.90 parts by weight of tetraoleic acid-POE(60) sorbitol, 0.10 parts by weight of sorbitan monooleate, a suitable amount of preservatives, and 10.00 parts by weight of ethanol were mixed, and dissolved under stirring at 50° C. Then the obtained solution was added in small portions to the previously-prepared aqueous solution, and mixed under stirring at 50° C. until the mixture became homogeneous. The temperature of the solution was lowered under stirring from 50° C. to 30° C., where the stirring was stopped. Suitable amount of flavoring agents and purified water were added to increase the total amount to 100 parts by weight. Then the mixture was stirred again into a homogeneous mixture to prepare a skin lotion.

Preparation Example 2

10.00 parts by weight of squalene and a suitable amount of preservatives were mixed, purified water was added to increase the total amount to 70.00 parts by weight, and the resulting mixture was heated to 80° C. to prepare solution (1). On the other hand, 0.10 parts by weight of carboxyvinyl polymer and 0.20 parts by weight of xanthan gum were dissolved in a suitable amount of purified water under stirring at room temperature to prepare solution (2). 0.10 parts by weight of triethanolamine, 5.00 parts by weight of 1,3-butylene glycol, and 0.01 parts by weight of the compound purified in Example 1 were dissolved in a suitable amount of purified water under stirring at room temperature to prepare solution (3). Further, 2.00 parts by weight of sodium hyaluronate was dissolved in a suitable amount of purified water under stirring at room temperature to prepare solution (4).

Next, solution (1) was added in small portions into a suitable amount of purified water, and mixed under stirring at 80° C. Solution (2), and then solution (3) were successively added under stirring. When mixed homogeneously, the mixture was cooled to 50° C. under stirring, where solution (4) was added, and purified water was added to increase the total amount to 100 parts by weight. The resulting solution was stirred again until the temperature was lowered to 30° C., where the stirring was stopped, to obtain a homogeneous emulsion.

Prescription Example 3

2.00 parts by weight of POE(20)sorbitan monostearate, 0.50 parts by weight of POE sorbitan tetraoleate, 0.50 parts by weight of glyceryl monostearate, 7.00 parts by weight of stearic acid, 3.00 parts by weight of cetyl alcohol, 3.00 parts by weight of cetyl palmitate, 7.00 parts by weight of jojoba oil, 3.00 parts by weight of paraffin, 0.01 parts by weight of the compound purified in Example 1, and a suitable amount of preservatives were mixed, and dissolved under stirring at 80° C. to prepare solution (1). On the other hand, 7.00 parts by weight of 1,3-butylene glycol and 62 parts by weight of purified water were mixed, and dissolved under stirring at 80° C. to prepare solution (2).

Then solution (1) was added in small portions into solution (2), emulsified, and cooled under stirring to 40° C., where the stirring was stopped, to prepare a homogenous cream.

Prescription Example 4

54.00 parts by weight of granulated sugar was dissolved in a suitable amount of purified water, mixed with 41.70 parts by weight of starch syrup, heated, and boiled down. Then 1.00 parts by weight of citric acid and 0.30 parts by weight of flavoring agents were added in small portions under homogenous stirring, cooled down to 90° C. under stirring, mixed with 0.01 parts by weight of the compound purified in Example 1, and stirred. The resulting homogenous mixture was molded by conventional means to obtain candies.

Prescription Example 5

32.00 parts by weight of sugar was added in small portions to 65.00 parts by weight of strawberry fruit, and heated under stirring to boil down. When the sugar concentration exceeded 65%, the heating was stopped, and 0.02 parts by weight of the compound prepared in Example 1, 0.15 parts by weight of citric acid, and a suitable amount of flavoring agent were added and mixed homogenously. The resulting concentrate was packed in a bottle while hot, sterilized, and rapidly cooled to prepare jam.

What is claimed is:

1. A compound of not less than 90% by weight purity represented by the formula (1):

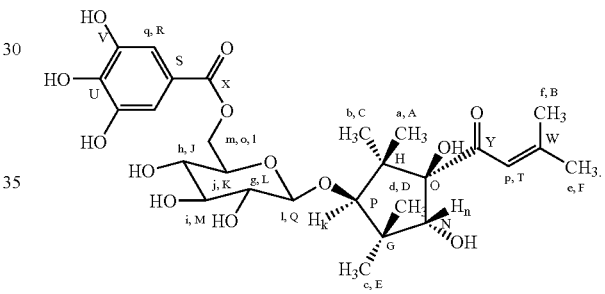

2. A method for producing the compound of claim 1, comprising preparing an extract from one or more materials selected from the group consisting of camu camu fruit juice, camu camu fruit pericarp, camu camu seeds, and mixtures thereof using at least one of water and an organic solvent; and purifying the extract.

3. An antioxidant comprising the compound of claim 1 as an active component.

4. A whitening agent comprising the compound of claim 1 as an active component.

5. A skin preparation for external use comprising at least one of the antioxidant of claim 3 and the whitening agent of claim 4.

6. A cosmetic comprising at least one of the antioxidant of claim 3 and the whitening agent of claim 4.

7. Food comprising the antioxidant of claim 3.

* * * * *

Disclaimer

7,074,907 B2 - Kenichi Nagamine; Miki Hayashi, both of Tokyo (JP); Kaori Yamasaki, Nagasaki, (JP). COMPOUND, PROCESS FOR PRODUCING THE SAME AND SUE THEREOF. Patent dated July 11, 2006. Disclaimer filed August 5, 2021, by the assignee, Nichirei Biosciences Inc.

I hereby disclaim the following complete claim 1-7 of said patent.

*(Official Gazette, August 23, 2022)*